United States Patent [19]

Daikuzono

[11] Patent Number: 5,193,526
[45] Date of Patent: Mar. 16, 1993

[54] LASER LIGHT IRRADIATION APPARATUS

[75] Inventor: Norio Daikuzono, Chiba, Japan

[73] Assignee: S.L.T. Japan Co., Ltd., Tokyo, Japan

[21] Appl. No.: 905,235

[22] Filed: Jun. 29, 1992

Related U.S. Application Data

[63] Continuation of Ser. No. 575,905, Aug. 31, 1990, abandoned.

[30] Foreign Application Priority Data

Sep. 5, 1989 [JP] Japan .................................. 1-230195

[51] Int. Cl.$^5$ ............................................. A61B 17/22
[52] U.S. Cl. ........................................ 128/7; 606/15; 606/16; 606/7; 128/398
[58] Field of Search ........................... 606/2, 7, 10–17; 128/395–398

[56] References Cited

U.S. PATENT DOCUMENTS

| | | |
|---|---|---|
| 4,233,493 | 11/1980 | Nath . |
| 4,660,925 | 4/1987 | McCaugham, Jr. ............. 350/96.15 |
| 4,693,244 | 9/1987 | Daikuzono . |
| 4,693,556 | 9/1987 | McCaughan, Jr. ................. 350/320 |
| 4,736,743 | 4/1988 | Daikuzono . |
| 4,799,479 | 1/1989 | Spears . |
| 4,832,979 | 5/1989 | Hoshino . |
| 4,848,339 | 7/1989 | Rink et al. . |
| 4,860,743 | 8/1989 | Abela . |
| 4,862,886 | 9/1989 | Clarke et al. ............................ 606/7 |
| 4,994,060 | 2/1991 | Rink et al. ............................ 606/28 |

FOREIGN PATENT DOCUMENTS 2185188 7/1987 United Kingdom .

OTHER PUBLICATIONS

"The Application of YAG Laser to Hyperthermia", Japan Society of Laser Medicine, by Takuo Nobori et al., vol. 6, No. 3, pp. 71–76.

"Endoscopic Local Hyperthermia with Nd-YAG Laser Experimental Study and Development of Computed Thermo System", Japan Society of Laser Medicine, by Sohtaro Suzuki, vol. 6, No. 3, pp. 347–350.

"Basic Stody on Photochemical Effect of Pheophorbide a Irridated by Nd:YAG Laser Light", Japan Society of Laser Medicine, by Shinro Mashiko et al., vol. 6, No. 3, pp. 113–116.

Dougherty et al., "Photoradiation Therapy for the Treatment of Malignant Tumors," *Cancer Research,* vol. 38, Aug. 1978, pp. 2628–2635.

*Primary Examiner*—Peter A. Aschenbrenner
*Attorney, Agent, or Firm*—Lowe, Price, LeBlanc & Becker

[57] ABSTRACT

A laser light irradiation apparatus used for medical treatment of living tissues. According to a preferred embodiment, the apparatus comprises a probe and a plural number of optical fibers. The optical fibers surround the axis of the probe. Laser light goes through each optical fiber and is applied to the probe. Then, the laser light is emitted from the probe to uniformly irradiate the tissues, and if desired, against the tissues over a broad area. Further, a guide wire and/or a lead wire for detecting a temperature can be placed so as to be coaxial with the probe. Therefore, a perforation of a normal part of the blood vessel can be prevented.

17 Claims, 8 Drawing Sheets

温度
44°C
42°C

LASER LIGHT IRRADIATION APPARATUS

This application is a continuation of application Ser. No. 07/575,905 filed Aug. 31, 1990 now abandoned.

BACKGROUND OF THE INVENTION

1. Field of the Invention

This invention relates to a laser light irradiation apparatus, which irradiates laser light to living tissues of an animal such as a human body for use an incision, vaporization of the living tissues or a thermal therapy and in case of widening a narrow path of the living tissues such as a stricture part caused by cholesterol formed in the blood vessel of the human body.

2. Prior Art

Medical treatments such as incisions of living tissues of animal organisms by irradiation with laser light are now conspicuous due to the ability of hemostasis.

It had been the conventional method that the laser light was irradiated from the fore end of an optical fiber retained out of contact with the living tissues. But this method causes severe damage to the fore end portion of the optical fiber. Therefore, a method using a contact probe which has been utilized lately is as follows:

First, laser light is transmitted into an optical fiber, whose fore end portion locates adjacent to treated living tissues. Next, the laser light fed out from the optical fiber is fed into an emitting probe, which may or may not contact the living tissues. Then, the laser light is emitted from the surface of the probe to be irradiated against the living tissues. In this case, the probe should be brought into contact with the living tissues (hereafter "living tissue" is sometimes expressed by "tissue" only).

The Applicant developed many kinds of contact probes which are utilized for various purposes.

On the other hand, Applicant proposed in Japanese Patent Application No. 63-171688, (Laid-Open No. 2-34161) a laser light medical treatment equipment for burning off a stricture part caused by cholesterol formed on the inner wall of a blood vessel.

Before this invention, that is Japanese Patent Application No. 63-171688, for the treatment for the stricture part, a heat wire probe was inserted into the stricture part. Then, since the heat wire probe was heated as a whole, there was a risk that a normal blood vessel other than the stricture part was damaged. Therefore, in order to prevent the normal blood vessel from being damaged, the laser light medical treatment equipment of this invention was proposed. According to this equipment, while a laser light emitting probe is progressed through the blood vessel to locate before the stricture part formed in the blood vessel, the laser light is emitted so as to be irradiated against only the stricture part, which is beyond the probe.

Further, lately, a localized thermal therapy is drawing special attention as a carcinostatic therapy. According to this method, cancer tissues are destroyed by keeping the cancer tissues at a temperature of about 42°–44° C. for 10–25 minutes by laser light irradiation. The effectiveness of this method has been reported by the inventors in the bulletin of Japan Society of Laser Medicine, vol. 6, No. 3 (January 1986), pp. 71–76 & 347–350.

On the other hand, considerable attention has been paid to laser-chemical therapies including the method reported in 1987 by Dougherty et al of the United States. According to this method, 48 hours after an intravenous injection of a hematoporphyrin derivative (HpD), weak laser-light such as argon laser or argon pigment laser is irradiated against a target area of the treatment. Whereupon oxygen of the primary term which has a strong carcinostatic action is produced by HpD. Since then, there have been published various reports in this regard, including the one in the bulletin of Japan Society of Laser Medicine, vol. 6, No. 3 (January 1986), pp 113–116. In this connection, it has also been known in the art to use "pheophobide a" as a photo-reactant. Further, recently, YAG laser has been put into use as a laser-light source.

In the above mentioned medical treatment, it is important that the laser light is irradiated uniformly for the cancer tissues and, in case of the thermal therapy, it is particularly important that the cancer tissues are heated uniformly.

Further, for heating the tissues uniformly, the Applicant disclosed in Japanese Patent Application Laid-Open No. 63-216579, that an apparatus has plural number of laser light emitters and an equipment for adjusting the power level of the laser light impinging into the emitters.

If laser light is irradiated against the tissues from an optical fiber directly or through the intermediary of a contact probe, the power level of the laser light irradiated against the tissues is the largest at a center position of an irradiated area on the surface of the tissues. The center position is contacted by the center of the optical fiber or that of the contact probe, then, the power level is lowered as a position on the surface of the tissues parts away from the above mentioned center position.

For example, as shown in FIG. 8, when the laser light is irradiated against the tissues M with a contact probe P, in the temperature distribution of this figure, there is a peak at its center position and in the both sides in relation to this peak, the level is lowered gradually away from this peak. If the power level of the laser light is raised, the size of this temperature distribution is also enlarged to be a substantial similar figure. However, the power level of the laser light is increased to an excess level, the tissues corresponding to the peak of the temperature distribution are damaged seriously. Accordingly, it is impossible to enlarge an irradiation area by only adjusting of the power level of the laser light.

Therefore, it is difficult to irradiate the laser light uniformly, and particularly more difficult to irradiate the laser light uniformly against the tissues having broad area. Accordingly, within the limit of the predetermined power level of the laser light, laser light irradiation against each small part of the tissues should be repeated many times in order to carry out the irradiation against all of the treated tissues over a broad area. As a result, a medical operation cannot be carried out quickly.

Under these circumstances, as described before, the Applicant proposed in Japanese Patent Application Laid-Open No. 63-216579 that the plural number of probes as the laser light emitters are provided and the laser light is irradiated from each probe simultaneously.

Although the laser light can be irradiated against the tissues having a broad area to some degree by provision of the plural number of laser light emitting probes, the necessity of a number of probes causes the following problem.

For forming the uniform temperature distribution on the irradiated tissues, the probes should be located at precise positions respectively so as to be contacted with the tissues uniformly. Therefore, the medical operation cannot be carried out quickly due to difficulties in precisely locating the probes. On the other hand, since each optical fiber should correspond to each probe, the size of the apparatus is large. Accordingly, this apparatus cannot be used for a medical treatment in a narrow path in the tissues such as a catheter in a blood vessel.

On the other hand, in case of a treatment for a so-called angio-plasty, which means burning off the stricture part formed on the inner surface of the blood vessel to widen the inside of the blood vessel, as described before, the Applicant proposed the laser light irradiation probe. In this case, the probe can be used instead of the conventional heat wire probe and is inserted into the blood vessel along the flexible guide wire, which was inserted into the blood vessel previously. Further, in an embodiment of this proposal, in order to prevent the guide wire from being damaged by the laser light irradiation, the guide wire is placed so as to be deflected from the axis of the probe.

However, as shown in FIG. 13, deflection of the guide wire in relation to the axis of the probe causes the following problem. When a probe P is progressed in the blood vessel until the probe P reaches at a bending part, due to the deflection of the guide wire, the probe P should be forced further in the blood vessel against the original bending part. Therefore, the bending manner at this original bending part of the blood vessel is set to be changed to another bending manner. In this case, when the laser light is irradiated against the stricture part m, there is the risk of breaking of the wall of the normal part of the blood vessel BV other than the stricture part m or so-called perforation there.

The energy districution of the laser light irradiation from the probe and the above mentioned temperature distribution shown in FIG. 8 have a common characterization. That is to say, there is a peak at its center position and at both sides in relation to this peak, the power level of laser light irradiation is lowered. Therefore, while the center of the stricture part m is completely burnt off, the inner wall of the stricture part m, which is away from the center, often still remains not burnt off. Accordingly, the power level of the laser light should be raised in order to burn off the whole stricture part completely. However, if a normal part of the inner wall of the blood vessel faces the center of the emitting face of the probe due to the bending of the blood vessel, there is a risk that the normal part of the vessel may be burned during treatment.

SUMMARY OF THE INVENTION

It is therefore a main object of the present invention to provide a small-sized laser light irradiation apparatus, by which laser light can be irradiated against living tissues uniformly, if desired, against the living tissues having a broad area, and in which a guide wire and a lead wire detecting a temperature are provided so as to be coaxial with a penetrating member for preventing the perforation at the normal part of a narrow path having bending parts.

In order to solve the above mentioned problems, a laser light irradiation apparatus of the present invention comprises a laser light transmissive emitting member and a plural number of laser light transmitting members. The transmitting members are provided so as to surround the axis of the emitting member. Then, laser light goes through each transmitting member so as to be fed into the emitting member and its fore end portion is buried in the transmissive material of the emitting member or adjacent to the impinging face of the emitting member.

According to the present invention, the plural number of laser light transmitting members, usually optical fibers, are placed to surround the axis of the laser light emitting member (this member hereinafter sometimes will be expressed by a probe). Therefore, for example, as shown in FIG. 6, in each power level of laser light irradiation from the emitting face of the probe, there is a peak at each axis of each optical fiber. That is to say, as shown in FIG. 7, a whole power level distribution, which is produced by combining each power level distribution, shows a uniform and broad power level distribution.

For the angio-plasty in the conventional art, only the stricture in the center part of a blood vessel was mainly burnt off. However, by the present invention, the laser light is emitted also from the circumferential part of the fore end face of the probe. Therefore, the material of the stricture along the inner wall of the blood vessel as well as the center part thereof can be burnt off effectively. Due to this complete burning, laser light emission with the high power level is not required. Further, even if the blood vessel is bent, thereby, the normal part of the inner wall of the blood vessel facing the center position of the emitting face of the probe, since the power level of the laser light irradiation is not so high, there is not fear of perforation at the normal part of the blood vessel.

In thermal therapy, since the tissues having a broad area are heated uniformly, this therapy can be performed quickly and there is no risk that the tissues at a center part of the irradiated area are seriously damaged seriously.

Further, while plural number of pairs of optical fibers and probes were provided in the conventional apparatus, in the apparatus of the present invention, a plural number of optical fibers correspond to one probe. Accordingly, although this apparatus also has a plural number of optical fibers, the size of this apparatus is smaller than the conventional apparatus. Therefore, the apparatus can be inserted into a narrow path of organisms.

On the other hand, by forming a through-hole along the axis of the probe, the laser light is not emitted from a center part of the fore end face of the probe. Accordingly, from the view of the whole power level distribution of the laser light irradiation, the laser light is emitted more uniformly. Further, the guide wire can be inserted through the through-hole; thus, the guide wire can be provided at the center of the probe. Therefore, when the probe is inserted along the guide wire, the probe can be always set to locate at the center of the blood vessel as shown in FIG. 1. Therefore, the blood vessel is not forced to be bent, thereby, the perforation, which might be caused due to the bending of the blood vessel by the laser light irradiation against the normal part of the blood vessel, does not occur.

With this apparatus, the thermal therapy can be also performed efficiently. That is to say, the lead wire detecting the temperature such as a thermocouple can be inserted through the through-hole so that the tip end of the lead wire can be pushed into the center of the target area to detect the temperature there for the efficient thermal therapy. However, in the prior art, since the thermocouple was provided so as to pass around and attach along the side of a probe, the thermocouple was set to be inserted into a position deflected from the center of the irradiated target area. Comparing the prior art, in the present invention, as described above, the thermal therapy can be performed under the precise temperature control due to the suitable location of the lead wire.

Particularly, in the case of thermal therapy, high power level of the laser light is not required. Therefore, the material of the probe is not required to have a high heat resistance.

Almost all of the probes, which had been invented by applicant, are fabricated from a ceramic material such as sapphire and the like. In order to scatter the laser light with the conventional probes, only two methods, in which the surface of each probe was roughened or a laser light scattering surface layer was provided on the surface of each probe, can be found.

Since the probe fabricated from the ceramic material is excellent in heat resistance, the probe can be used effectively when heat resistance is required. However, when the tissues are heated in the above mentioned thermal therapy and the like, the high power level of the laser light is not required, that is to say, the probe can be worked sufficiently with the low power level of the laser light.

As the result of research by Applicant, a synthetic resin material is found to be used for the probe in the present invention. Then, by fabricating the synthetic resin material containing laser light scattering particles to be a predetermined shape, the laser light fed into the probe is scattered with the scattering particles in the probe. Therefore, the laser light is emitted in various directions from the surface of the probe. This produces a large area of laser light irradiation. Further, since the probe is fabricated from the synthetic resin material, the probe has also an advantage that it can be formed to be many types of suitable shapes according to its usage.

Then, the probe can be formed from the synthetic resin material so that the lead wire detecting the temperature such as the lead wire having the thermocouple at its tip end can be inserted through the probe. In this case, the temperature is required to be detected at a position which exists inside of the tissues and which is adjacent to the fore end of the probe being brought into contact with the surface of the tissues. Then, according to the present invention, detecting the temperature can be carried out precisely due to the suitable location of the lead wire. However, in the prior art, the temperature at the above mentioned precise position cannot be detected for the following reasons:

In the prior art, it has been known that the lead wire is provided separately with the probe. Therefore, the thermocouple attached to the tip end of the lead wire is set to be pushed into the tissues at the side part of the probe. That is to say, the thermocouple cannot be set in the above mentioned precise position in the tissues due to the unsuitable location of the lead wire. Accordingly, it is impossible to detect the temperature precisely. Alternatively, it has been known that the lead wire is passed around the side surface of the probe and the tip end of the lead wire is attached to the tip end of the probe. By this method, the temperature at a point on the surface of the tissues adjacent to the external surface of the fore end portion of the contacted probe can be detected. However, the detected temperature is that of the surface of the tissues or is not that of the inside of the tissues. As a result, by these conventional methods, it is impossible to detect the temperature at the precise position. Thus, the temperature control for heating the tissues can not be performed surely.

In the present invention, since the probe is fabricated from the synthetic resin material, the through-hole can be formed along the axis of the probe and the lead wire can be inserted through the probe to fix the wire integrally to the probe by molding. Then, the lead wire is projected from the external surface of the fore end portion of the probe. Accordingly, when the probe is brought into contact with the surface of the tissues, the projecting portion of the lead wire can be pushed into the tissues together with the fore end portion of the probe. Therefore, the temperature at the precise position, which is adjacent to the external surface of the fore end portion of the probe and which exists inside of the tissues, can be detected. As a result, this apparatus is excellent in temperature control for heating the tissues.

Further objects and advantages of the present invention will be apparent from the following description, reference being had to the accompanying drawings wherein preferred embodiments of the present invention are clearly shown.

DESCRIPTION OF THE PREFERRED EMBODIMENTS

Now, the present invention is described more particularly with several kinds of embodiments.

Figure 1:
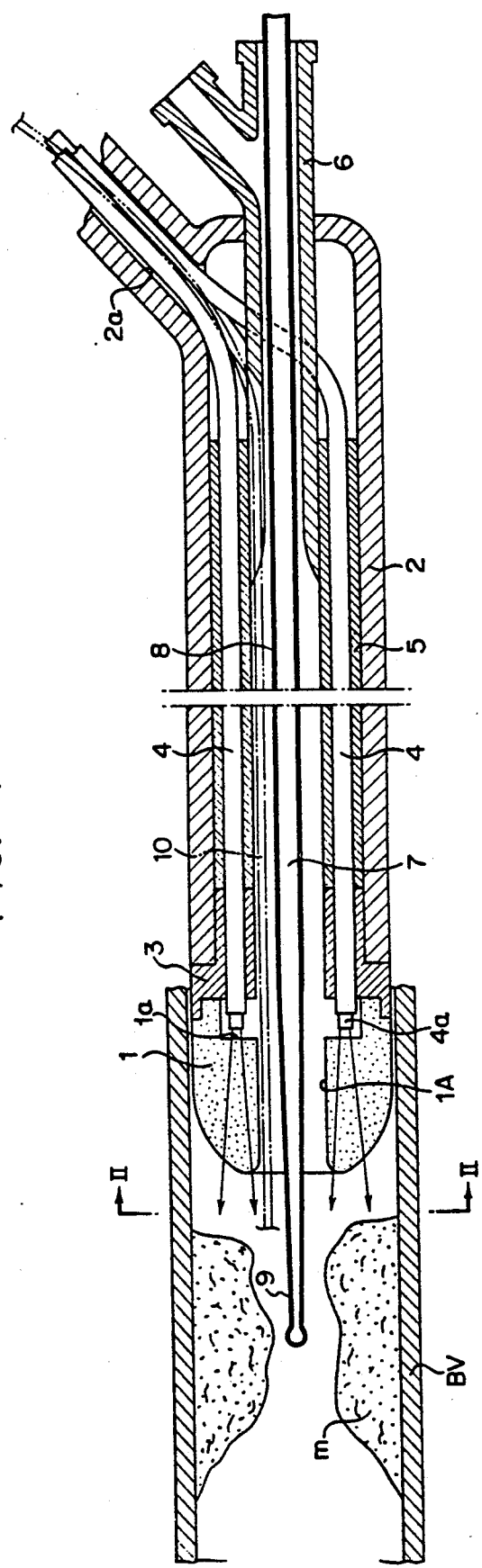
FIG. 1 is a longitudinal sectional view of an important part of an irradiation apparatus in a first embodiment related to the present invention.
Figure 2:
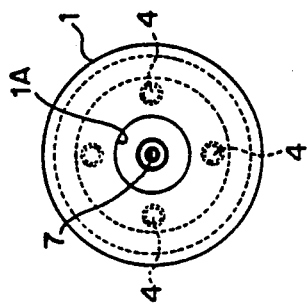
FIG. 2 is a sectional view taken on line II—II of FIG. 1.

FIGS. 1 and 2 show a first embodiment mainly for an angioplasty. A probe 1 is fabricated from a synthetic resin material or ceramic and so on. The fore end face of the probe 1 is rounded off at its circumference in order to decrease the friction caused by proceeding of the probe in a blood vessel at the inner wall of the vessel. A main tube 2 is provided so as to be coaxial with the probe 1 and is fabricated from a flexible material such as the resin of tetrafluorethylene and the like. The probe 1 and the main tube 2 are connected through the intermediary of a metal holder 3.

In the main tube 2, a plural number, four for example in FIG. 1, of optical fibers 4 are provided in parallel to each other and surrounding the axis of the probe 1 and/or the axis of the main tube 2. Each optical fiber 4 is connected to a laser light generator (not shown). Each tip portion of the optical fiber 1 is exposed to a core 4a. Each core 4a is adjacent to the back end face or the impinging face 1a of the probe 1. Each optical fiber 4 is inserted into the main tube 2 from an inserting hole 2a. Then, the fore end portion of the optical fiber 4 is supported and surrounded by the holder 3. The base portion of the back side portion of each optical fiber 4 in the main tube 2 is supported and surrounded by a synthetic resin holder tube 5.

On the other hand, a through-hole 1A is formed to go through along the axis of the probe 1 to communicate with the inner through-hole of the holder 3 and the holder tube 5. A conductive tube 6 is provided in the main tube 2 so as to be projected from the back end of the main tube 2. The tip end of the conductive tube 6 is inserted into the inner side of the holder tube 5. A guide wire 7 is inserted through the conductive tube 6, further through the inner side of the holder tube 5 and that of the holder 3 so as to be projected from the through-hole 1A of the probe 1. The base side portion of the guide wire 7 is coated by a synthetic resin coating such as the resin of tetrafluorethylene. The fore end portion of the guide wire 7 is tapered gently and is totally gold plated. The guide wire 7 has a spherical tip end. A lead wire 10 detecting a temperature, which is used not for the angio-plasty but for a thermal therapy, is inserted through this apparatus.

This laser light irradiation apparatus is used as follows:

Before the apparatus is introduced into the human body, the guide wire 7 is inserted through the apparatus. Next, the guide wire 7 is further inserted into the treated blood vessel BV so that the tip end of the guide wire 7 extends further than a stricture part m, which will be burnt off by laser light irradiation.

Then, the apparatus other than the guide wire 7 is inserted in the blood vessel BV along the guide wire 7 so as to proceed until the external surface of the fore end portion of the probe 1 is adjacent to the stricture part m. Laser light is fed into each optical fiber 4 to be emitted from the core 4a of the optical fiber 4. The emitted laser light receiving into the impinging face of the probe 1, passes through the body of the probe 1, and is emitted from the front surface of the fore end portion of the probe 1. Finally, the laser light is irradiated against the stricture part m.

Figure 4:
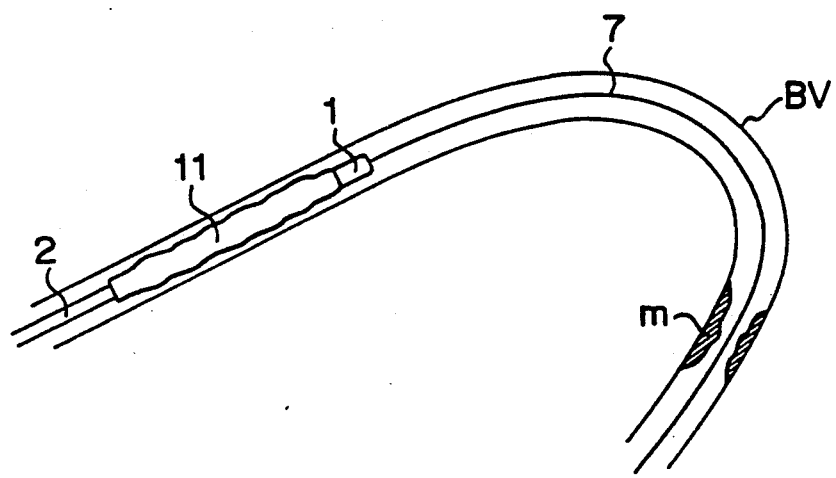
FIG. 4 is an illustration showing an operation of an irradiation apparatus being inserted into a blood vessel.

By the laser light irradiation, the stricture part m is burnt off to widen the inside of a blood vessel. If desired, as shown in FIG. 4, pressurized air or pressurized liquid is sent into a balloon 11 connected between a probe 1 and a main tube 2, thus, the balloon 11 is expanded and press the stricture part m. As a result, together with the above mentioned burning off the inside of the blood vessel by the laser light irradiation, the stricture part m can be broken mechanically.

As shown in FIG. 1, in the present invention, the laser light is emitted from the circumference of the fore end face of the probe 1. Therefore, the laser light is irradiated efficiently against the stricture part m formed on the inner wall of the blood vessel BV. Accordingly, the stricture part m can be burnt off sufficiently even if the power level of the laser light is low.

When the laser light is irradiated against the stricture part m, the laser light is irradiated against also the projecting part of the guide wire 7. Therefore, the surface of the fore end portion of the guide wire 7 is coated by a gold plating layer 9 for preventing the surface from being damaged.

Figure 3:
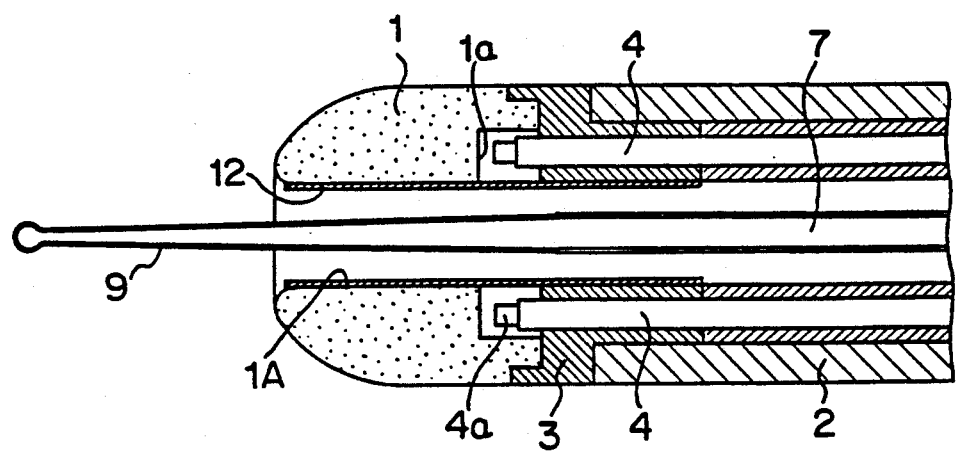
FIG. 3 is a longitudinal sectional view of an important part of an irradiation apparatus, which is modified from the first embodiment.

As shown in FIG. 3, if desired, a reflecting sleeve-like tube 12 fabricated from a thin metal is provided on the inner side surface of a through-hole 1A and a laser light reflecting layer such as a gold plated layer is formed on the surface of the sleeve-like tube 12. Accordingly, laser light is reflected on the gold plated layer. Therefore, laser light irradiation toward the axis of a probe 1 can be decreased.

Figure 5:
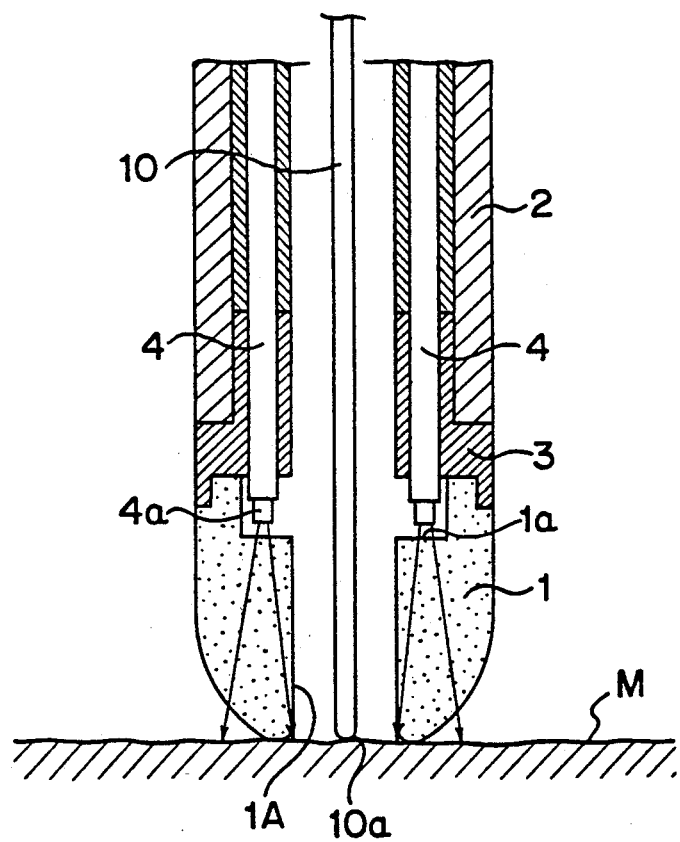
FIG. 5 is a longitudinal sectional view of an important part of an irradiation apparatus carrying out a local thermal therapy for cancer tissues.

The apparatus of the type described above is used for also the thermal therapy efficiently. As shown in FIG. 5, a lead wire 10 detecting a temperature having a thermocouple 10a at its tip end is brought into contact with the surface of cancer tissues M or is pushed into the cancer tissues M. Then, the probe 1 is brought into contact with the surface of the cancer tissues M. As a result, the laser light having a low power level is irradiated against the tissues M from each optical fiber 4 through the intermediary of the probe 1. In this case, the power level of the irradiated laser light can be controlled so as to keep the tissues M at the temperature of about 42°-44° C.

Figure 6:
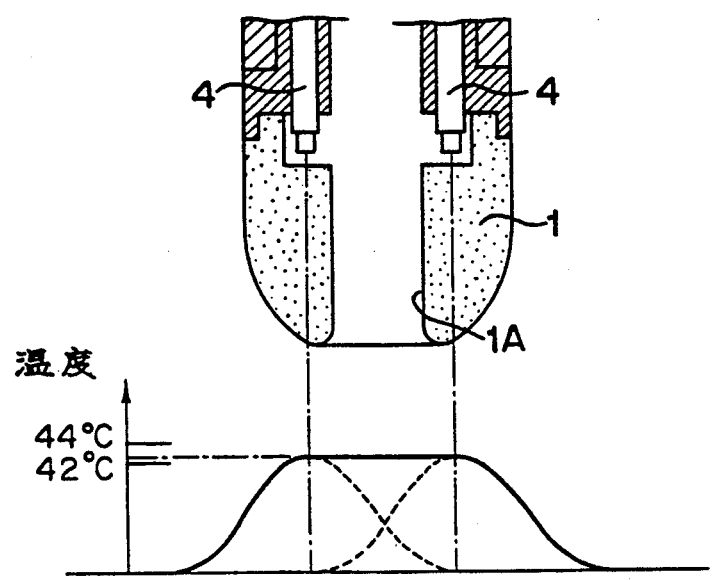
FIG. 6 is a schematic illustration for a temperature distribution with the apparatus of FIG. 5.
Figure 7:
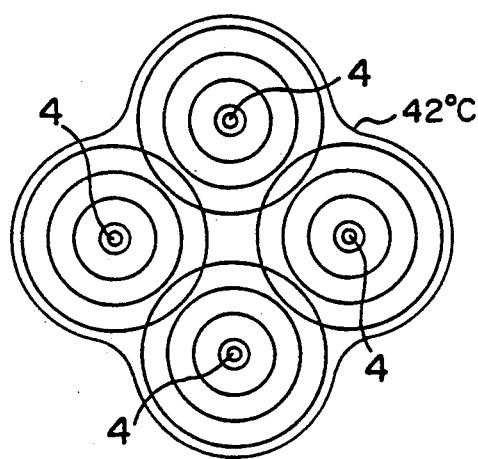
FIG. 7 is a plan view of the temperature distribution of FIG. 6.
Figure 8:
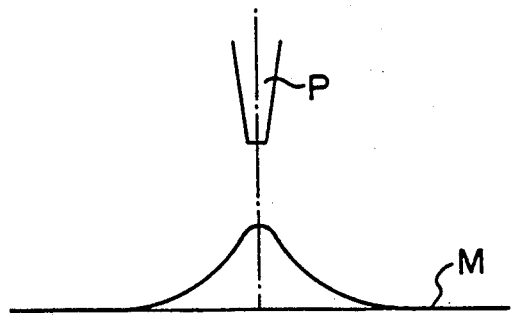
FIG. 8 is a temperature distribution with a conventional apparatus.

As described above, the laser light is irradiated against the tissues M from the fore end circumferential face of the probe 1, as shown in the temperature distribution of FIGS. 6 and 7, comparing the temperature distribution of FIG. 8 with the conventional apparatus, the temperature can be controlled uniformly over a broad area.

Although the through-hole 1A is not always necessary, the through-hole 1A is preferably provided in the apparatus to give the uniform temperature distribution.

For example in FIG. 5, since the through-hole 1A is provided, the laser light, which reaches at the inner side surface of the through-hole 1A, is partly refracted to penetrate through the through-hole 1A and partly reflected to go toward the tip end of the apparatus. Comparing an apparatus having no through-hole, in case of the apparatus having the through-hole, the rate of the emitted laser light from the fore end circumferential face of the probe 1 is more increased, thereby, more uniform temperature distribution is obtained.

Further, although the number of the provided thermocouple 10a is one in the apparatus of FIG. 5, a plural number of thermocouples are preferably provided which can contact several positions of the tissues M. Consequently, the temperature can be controlled more precisely.

According to the present invention, the probes having many kinds of shapes can be used in many kinds of manners.

Figure 10:
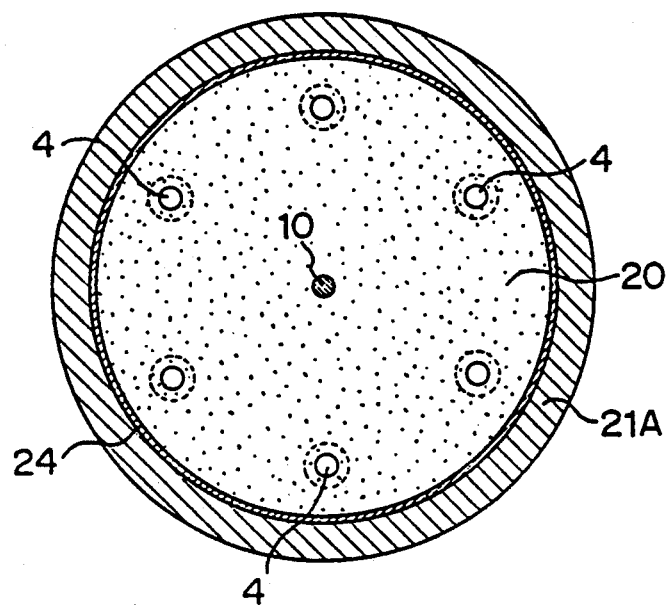
FIG. 10 is a sectional view taken on line X—X of FIG. 9.
Figure 9:
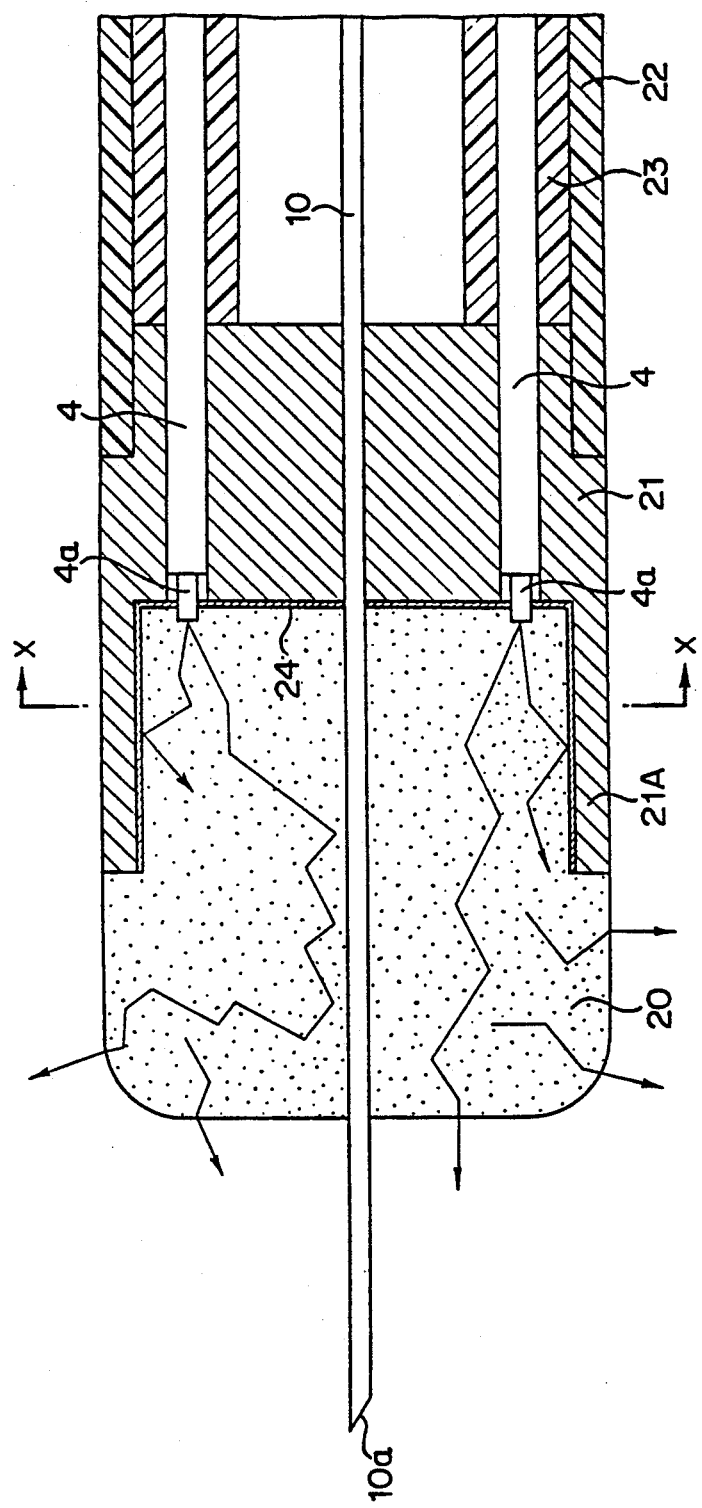
FIG. 9 is a longitudinal sectional view of an irradiation apparatus in another embodiment.

For example, as shown in FIGS. 9 and 10, a probe 20 fabricated from a synthetic resin material can be used. This probe 20 is connected to a flexible protection tube 22 fabricated from the resin of tetrafluorethylene and the like through the intermediary of a metal holder 21 having a sleeve-like connector 21A.

A supporting tube 23 fabricated from a synthetic resin material is provided to be connected to the holder 21 on the inner side surface of the protection tube 22. In the supporting tube 23, six optical fibers 4 are supported so as to surround the axis of the tube 23. Each optical fiber 4 is optically connected to a laser light generator (not shown). A lead wire 10 detecting a temperature having a thermocouple 10a at its tip end is inserted through the holder 21 and the probe 20 so as to project from the fore end portion of the probe 20. Then, the lead wire 10 is connected to a temperature measuring unit (not shown). Then, according to the result of detecting the temperature, the power level of the laser light, which is fed into the optical fiber 4 from the laser light generator, should be controlled. This controlling is carried out by, for example, adjusting a timer switch, which is provided between the laser light generator and the back end of the optical fiber 4. The probe 20 composes a substantially cylindrical part having a fore end face being rounded off at its circumference and another cylindrical part at the back side of the probe 20 having a smaller radius than that of the substantial cylindrical part by the thickness of the holder 21. These two cylindrical parts are fixed integrally. The smaller cylindrical part of the probe 20 is fitted in the sleeve-like connector 21A. Adding to this fitting, if desired, by using an adhesive between the mating surfaces; a back end circumferential face of the larger cylindrical part of the probe 20 and the fore end circumferential face of the sleeve-like connector 21A for high strength in fixing.

A laser light reflective layer 24 is formed on the mating surfaces of the probe 20 and the holder 21, in this embodiment the circle fore end face of the holder 21 and the inner side face of the sleeve-like connector 21A. Although the reflective layer 24 is preferably gold plated to give a high heat resistance, it might be aluminum plated and the like in view of the material of the layer. For forming the layer, vapor-deposit as well as plating can be used.

Further, the fore end portion of the optical fiber 4 is inserted to be buried in the material of the probe 20 and the fore end face of the core 4a of each optical fiber 4 is contacted with the material of the probe 20 directly without any gap.

The probe 20 of this embodiment contains laser light scattering particles and is fabricated from the laser light transmissive resin material. The material is synthetic resin such as silicone resin, acrylic resin (more preferably, methyl methacrylate resin), carbonate resin, polyamide resin, polyethylene resin, urethane resin, polyester resin and the like, more preferably, thermoplastic synthetic resin. For the laser light scattering particles, the material, which has a larger refractive index for the laser light than that of the above mentioned synthetic resin material of the probe, is used, for example, a natural or an artificial material such as diamond, sapphire, quartz material, single crystal zirconium oxide, laser light penetrating synthetic resin having heat resistance (it is needless to say that it is different from the above mentioned synthetic resin material of the probe), laser light reflective metal (such as gold, aluminum and the like), and the particles on whose surface the above mentioned laser light reflective metal are coated to be a compound material.

On the other hand, if desired, the probe contains laser light absorbing particles such as carbon, graphite, iron oxide, manganese dioxide and the like together with the scattering particles. A portion of laser light is scattered in the probe and emitted from the probe, but some of the laser light impinges on the absorbing particles to generate heat energy to give a large effect of heating.

The above mentioned probe 20 of this embodiment is fabricated by molding to a desired shape from the synthetic resin material, which is in a melted state and into which the scattering particles are dispersed. As a result, the fore end portion of the optical fiber 4 is buried in the material of the probe 20 as shown in FIG. 9 and the middle part of the lead wire 10 detecting the temperature is buried in the material of the probe 20 so as to be fixed integrally to the probe 20. Accordingly, for fabricating this apparatus, for example, the holder 21 is made easily by moulding from one mould to which the material is poured, while the optical fiber 4 and the lead wire 10 project from the circular fore end face of the holder 21.

The laser light irradiation apparatus of the type described above in the present invention is used, for example, in a following manner. The laser light is generated from the laser light generator, while the apparatus connected to an endoscope is surgically or physically inserted to a treated target area in a human body. The laser light from the laser light generator is fed into the back end of each optical fiber 4 and is transmitted therein to be emitted from the fore end face of the core 4a. Then, the emitted laser light is fed into the probe 20 directly and is penetrated therein to be emitted from its external surface, while the laser light is repeatedly refracted on the scattering particles in the probe 20. Therefore, as shown in FIG. 9, the laser light, after repeated refraction, is emitted from the external surface of the probe 20 uniformly for irradiating the tissues. As a result, as shown in FIG. 9, the laser light reaching the internal surface of the sleeve-like connector 21A is reflected on the reflection layer 24. Therefore, the sleeve-like connector 21A and the metal holder 21 are prevented from being heated and from being damaged, further, the reflected laser light is brought forward.

Laser light irradiation of this embodiment is carried out in the same manner as that of the embodiment shown in FIG. 5. That is to say, while the external surface of the fore end portion of the probe 20 is brought into contact with cancer tissues M, the projecting portion of the lead wire 10 from the external surface of the fore end portion of the probe 20, is pushed into the tissues M. Then, the temperature of the tissues M is detected with the thermocouple 10a for controlling the power level of the laser light fed into the optical fiber 4, in other words, the power level of the laser light emitted from the external surface of the probe 20, as described before. Then, the cancer tissues M are destroyed by keeping the tissues M at the temperature of about 42°-44° C.

On the other hand, the laser light also irradiates the lead wire 10 detecting the temperature in the probe 10. Therefore, in order to prevent the lead wire 10 from being heated and from being damaged, the wire 10 is preferably coated with a laser light reflecting layer such as a gold plated layer and a titanium coating layer like the laser light reflecting layer for the above mentioned guide wire 7 of FIG. 1.

Figure 11:
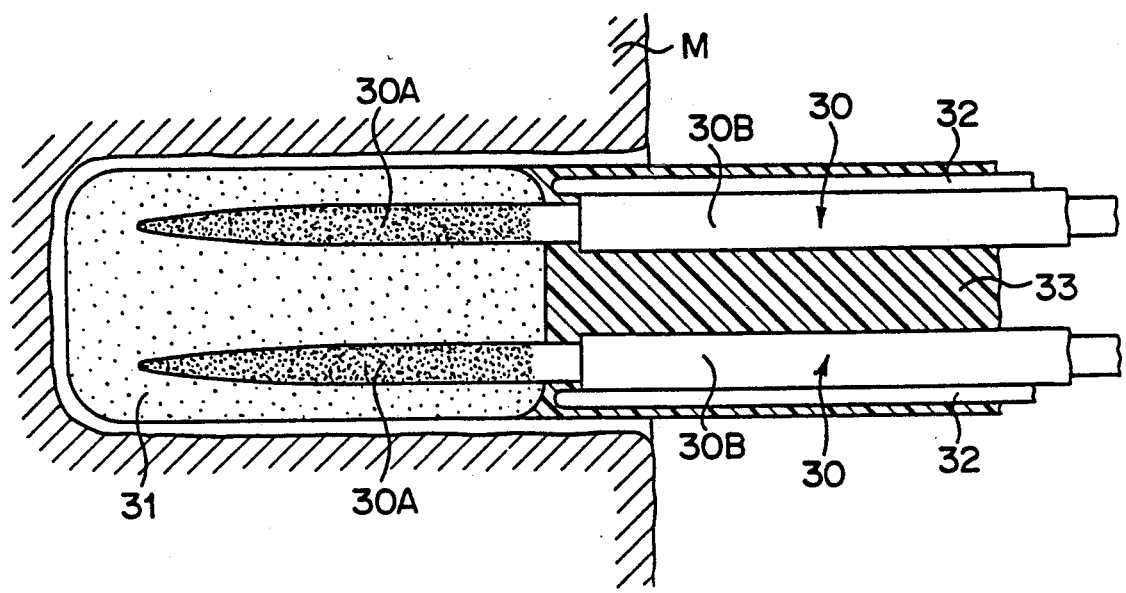
FIG. 11 is a longitudinal sectional view of an important part of an irradiation apparatus in another embodiment.

FIG. 11 shows another embodiment. The apparatus of this embodiment is used effectively in a treatment not for the surface of tissues but for inside of the tissues.

A probe 31 and plural number of optical fibers 30 are provided in this apparatus. At the fore end portion of each optical fiber 30, a clad 30B is removed so that a core 30A is exposed. The tip end of the core 30A is tapered. A laser light scattering layer is formed on almost all of the external surface of the core 30A. In this figure, this laser light scattering layer is illustrated by marking dots. For forming this scattering layer, first, ceramic powders such as silicon dioxide and the like are sprayed and heated to a temperature which is slightly lower than its melting point. Therefore, the original sprayed powders do not become homogeneous due to incomplete heating. Then, these incompletely heated ceramic powders are cooled. Accordingly, the laser light scattering layer can be formed on the core 30A, where the powders partly melt and partly remain. Due to this scattering layer, when the laser light is emitted from the external surface of the core 30A, the laser light impinges on each resulting ceramic powder with refraction to be scattered.

On the other hand, the probe 31 is provided so that the cores 30A, each of which is covered with this scattering layer, are buried in the material of the probe 31. The material of the probe 31 is fabricated from synthetic resin containing scattering particles in the same manner as the embodiment of FIG. 9.

Lead wires 32 detecting temperatures are provided to be connected to the cores 30B respectively. The external surface of each lead wire 32 is gold plated. Then, the tip end of each lead wire 32 locates adjacent to the back end face of the probe 31. The lead wires 32 together with the optical fibers 30 are surrounded by a flexible sheath 33, which is fabricated from synthetic resin such as polyethylene, urethane and the like, silicone rubber and so on. By moulding, the sheath 33 is fixed integrally to the lead wires 32, the optical fibers 30 and the probe 31.

Figure 12:
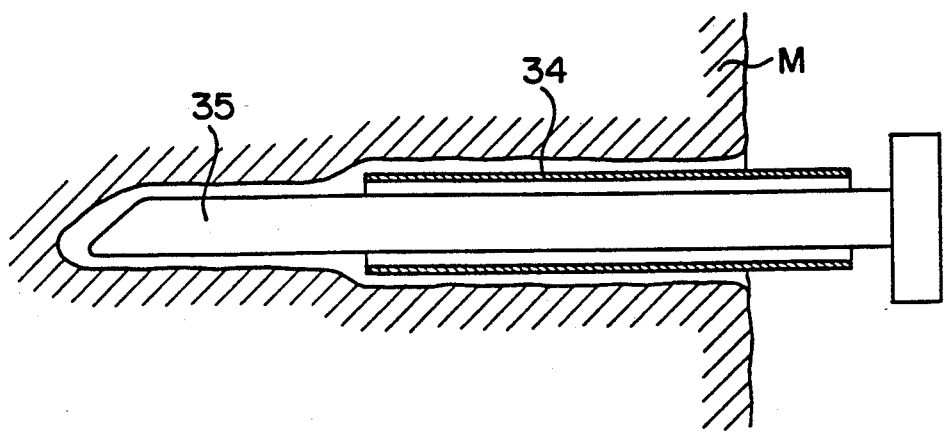
FIG. 12 is a longitudinal sectional view showing an operation for forming an inserting guide prior to inserting of the apparatus of FIG. 11 into living tissues.
Figure 13:
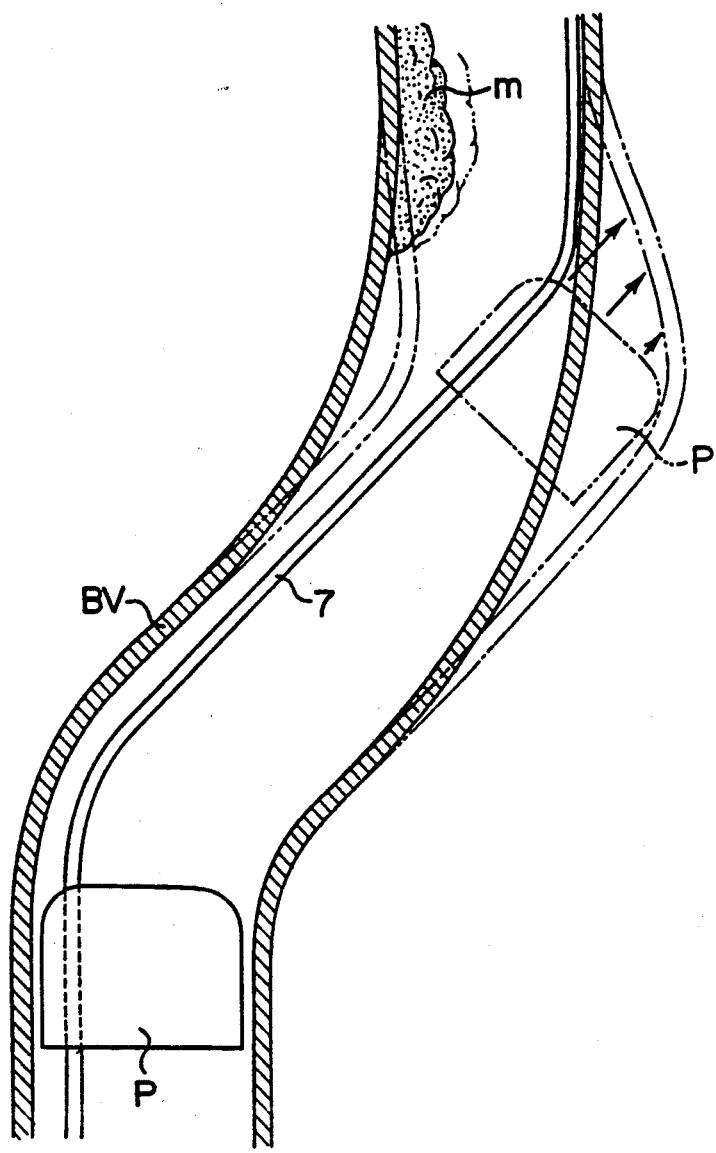
FIG. 13 is a longitudinal sectional view showing an embodiment of conventional plastic surgery for a blood vessel.

In case of applying this apparatus of this embodiment, as shown in FIG. 12, first, a so-called puncture needle 35 together with a guide tube 34 is inserted into the tissues M such as lever tissues. Next, only the puncture needle 35 is removed. Then, instead of the needle 35, the fore end portion of this laser light irradiation apparatus is inserted into the tissues M so as to go through the guide tube 34. Then, the laser light is fed into each optical fiber 30 to be emitted from each core 30A provided at the fore end portion of the optical fiber 30. As so doing, the laser light is scattered in the scattering layer covering each core 30A. Then, the scattered and emitted laser light is fed into the probe 31 and goes through it, while the laser light repeats to be scattered with the scattering particles in the probe 31. At last, the laser light is emitted from the external surface of the probe 31 uniformly. This apparatus is applied for a local thermal therapy for cancer tissues in a liver encephalic malignant tumors and cancer tissues in a breast.

The scattering particles contained in the scattering layer are basically the same as the above mentioned scattering particles in the probe. However, the particles, which cannot make a film when they melt, are not suitable, thus, ceramic particles are generally used for the scattering particles.

Further, if desired, surface layers might be formed on the surfaces of the above mentioned several kinds of probes or the surfaces of the above mentioned scattering surface layers covered on the cores 30A of FIG. 11 respectively to give a large scattering effect. This surface layer contains light scattering particles, which have a larger refractive index than that of the material of the probe or that of the above mentioned synthetic resin material. For example, sapphire, silicon dioxide, aluminum oxide and the like are used as the scattering particles. Then, the surface layer also contains laser light absorbing particles, which can be included in the probe as described before, such as carbon and the like. Finally, the surface layer contains a binder, which adheres the particles to each surface and forms a film on the surface as described hereinafter.

Due to the surface layer, the laser light is scattered by the light scattering particles, further, when the laser light impinges on the laser light absorbing particles, the greater part of the energy of the laser light is converted to heat energy.

As the vaporization of the tissues is accelerated, the tissues can be incised with the laser light having the low power level of energy penetrated into the probe. Therefore, when the tissues are incised, the probe can be moved rapidly. Further, since the required energy of the laser light penetrating into the probe is low, the medical operation can be carried out in short time with an inexpensive and small scaled laser light generator.

On the other hand, referring to the surface layer, if a dispersion containing the laser light absorbing particles and the light scattering particles was coated on the surface of the probe, after a vaporization of a dispersion medium, the contact of this probe with the tissues or other substances would cause a damage to the surface layer, because both kinds of particles are attached to the surface of the probe only by physical adsorptive power.

Therefore, by the binder which sticks the laser light absorbing particles and the light scattering particles to the surface of the probe, an adhesion of the surface layer to the probe is enhanced. In this case, the binder is preferably made of light penetrating particles such as synthetic resin particles or ceramic particles such as quartz particles and the like. For forming the film, when the synthetic resin particles are used as the material of the binder, the particles should be melted, or when the ceramic particles having a higher melting point than that of the probe are used, the surface of the probe should be melted.

Further, by forming a rough surface on the surface of the probe or by forming the above mentioned surface layer on the rough surface, the laser light can be irradiated more effectively, because the laser light is scattered on the rough surface when the laser light is emitted. If desired, the rough surface is formed on the above mentioned core 30A; further, the above mentioned scattering layer might be formed on this rough surface.

Although in the above mentioned embodiments shown in FIGS. 9 and 11, each core 4a or 30A of each optical fiber 4 or 30 is buried in the material of the probe 20 or 31, in other embodiments of the present invention, the fore end face of each optical fiber is located so as to be apart from the back end (impinging) face of each probe. In this case, impurities such as dusts and the like are produced in the gap; further, impurities are attached to the back end face of each probe and the fore end face of each optical fiber. Accordingly, since the laser light is impinged on the impurities, the back end face of the probe is heated. That is to say, the power level of the laser light fed into the probe is lowered. Therefore, if the probe is fabricated from the synthetic resin material thereby the optical fiber is molded to be fixed integrally to the probe easily, the fore end portion of the optical fiber is preferably embedded in the synthetic material of the probe.

While preferred embodiments have been described, it is apparent that the present invention is not limited to the specific embodiments thereof.

What is claimed is:

1. A laser light irradiation apparatus comprising:

a laser light emitting member;

a plurality of laser light transmitting members, located around an axis of said emitting member, wherein a fore end portion of each of the transmitting members couples laser light to said emitting member; and a lead wire for detecting a temperature, which extends through said light emitting member so as to project from a light emitting surface of the light emitting member.

2. An apparatus according to claim 1, wherein a through-hole is formed along the axis of said emitting member.

3. An apparatus according to claim 2, further comprising a flexible guide wire, for guiding said light emitting member, wherein said flexible guide wire is inserted through said through-hole.

4. An apparatus according to claim 2, wherein said lead wire for detecting a temperature is inserted through said through-hole.

5. An apparatus according to claim 3, further comprising at least one additional lead wire for detecting temperature wherein tip ends of said lead wires can be brought into contact with corresponding positions respectively in tissues said laser light is irradiated against.

6. An apparatus according to claim 1, further comprising means for adjusting power level of laser light transmitted through said laser light transmitting members in response to the detection of temperature via said lead wire.

7. An apparatus according to claim 2, wherein a reflecting layer is formed on an inner surface of said through-hole.

8. An apparatus according to claim 7, wherein said reflecting layer is a gold plated layer.

9. An apparatus according to claim 1, wherein said laser light transmitting members are optical fibers.

10. An apparatus according to claim 1, wherein at least the portion of said lead wire extending through and projecting from the light emitting surface of said light emitting member are coated with a laser light reflecting material.

11. An apparatus according to claim 1, further comprising a surface layer formed on the light emitting surface of said light emitting member, wherein said surface layer contains laser light absorbing particles, light scattering particles which have a larger refractive index than that of said light emitting member and a laser light transmissive material as a binder.

12. A laser light irradiation apparatus comprising:

a light emitting member;

at least one transmitting member, through which laser light is transmitted so as to be applied to the light emitting member; and a lead wire for detecting a temperature, which extends through the light emitting member so as to project from a light emitting surface of the light emitting member.

13. An apparatus as in claim 12, wherein a part of the lead wire which passes through the light emitting member is embedded in the material of the light emitting member.

14. An apparatus as in claim 12, wherein the light emitting member has a bore therethrough and said lead wire passes through the bore in the emitting member.

15. An apparatus as in claim 14, further comprising a reflective coating located on the inner surface of the bore through the light emitting member.

16. An apparatus as in claim 12, wherein said at least one transmitting member, comprises at least one optical fiber, an end of said at least one optical fiber being exposed and held adjacent to a light receiving surface of the light emitting member.

17. An apparatus as in claim 12, further comprising a reflective coating on said lead wire.

* * * * *